US009801980B2

(12) United States Patent
Karino et al.

(10) Patent No.: US 9,801,980 B2
(45) Date of Patent: Oct. 31, 2017

(54) POLYMER STENTS AND METHODS OF MANUFACTURE

(75) Inventors: Wataru Karino, Tustin, CA (US);
Steve Plotkin, Tustin, CA (US);
Gregory M. Cruise, Tustin, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 1164 days.

(21) Appl. No.: 13/332,048

(22) Filed: Dec. 20, 2011

(65) Prior Publication Data

US 2012/0187604 A1 Jul. 26, 2012

Related U.S. Application Data

(60) Provisional application No. 61/427,773, filed on Dec. 28, 2010, provisional application No. 61/425,175, filed on Dec. 20, 2010.

(51) Int. Cl.
| | | |
|---|---|---|
| B29C 45/08 | (2006.01) | |
| B29C 39/02 | (2006.01) | |
| B29C 39/24 | (2006.01) | |
| A61L 31/04 | (2006.01) | |
| B29C 39/00 | (2006.01) | |
| B29C 35/08 | (2006.01) | |
| A61L 31/14 | (2006.01) | |

(52) U.S. Cl.
CPC ............ *A61L 31/048* (2013.01); *A61L 31/14* (2013.01); *B29C 35/08* (2013.01); *B29C 39/006* (2013.01); *B29C 39/02* (2013.01)

(58) Field of Classification Search
None
See application file for complete search history.

(56) References Cited

U.S. PATENT DOCUMENTS

| | | | |
|---|---|---|---|
| 5,163,952 A | 11/1992 | Froix | |
| 5,292,802 A * | 3/1994 | Rhee et al. | ................ 525/54.1 |
| 5,935,506 A * | 8/1999 | Schmitz et al. | ............. 264/400 |
| 6,530,950 B1 * | 3/2003 | Alvarado | ............ A61K 9/0024 |
| | | | 526/319 |
| 2004/0005423 A1 * | 1/2004 | Dalton et al. | ............... 428/36.9 |
| 2005/0096729 A1 * | 5/2005 | Donadio | .................. A61F 2/91 |
| | | | 623/1.15 |
| 2006/0276875 A1 * | 12/2006 | Stinson | ..................... A61F 2/91 |
| | | | 623/1.15 |
| 2008/0319540 A1 * | 12/2008 | Jordan | .................... A61L 31/14 |
| | | | 623/1.49 |
| 2010/0004734 A1 * | 1/2010 | Ramzipoor et al. | ......... 623/1.15 |
| 2010/0262223 A1 * | 10/2010 | Kleiner | .................. A61L 31/06 |
| | | | 623/1.15 |

FOREIGN PATENT DOCUMENTS

| | | |
|---|---|---|
| WO | 2007/115208 | 10/2007 |
| WO | 2012/082440 A1 | 6/2012 |

\* cited by examiner

*Primary Examiner* — Matthew Daniels
*Assistant Examiner* — Kimberly A Stewart
(74) *Attorney, Agent, or Firm* — K&L Gates LLP; Louis C. Cullman; Georgia N. Kefallinos

(57) ABSTRACT

Methods of forming and/or manufacturing polymeric stents are disclosed. Polymeric stents are also disclosed.

9 Claims, 11 Drawing Sheets

POLYMER STENTS AND METHODS OF MANUFACTURE

CROSS REFERENCE TO RELATED APPLICATIONS

This application claims priority to and the benefit of U.S. provisional patent application No. 61/427,773, filed Dec. 28, 2010 and U.S. provisional patent application No. 61/425,175, filed Dec. 20, 2010, the entire disclosure each of which are incorporated herein by reference.

BACKGROUND

Stents are often implanted within a patient's vessel for therapeutic purposes such as maintaining the patency of the vessel or treating an aneurysm. Typically, stents are primarily composed of a metal or metallic alloy, such as Nitinol, stainless steel, or cobalt-chromium, which allows the stent to expand from a compressed configuration in a vessel. Generally, metals have remained the materials of choice for stent construction due to their mechanical properties and durability.

SUMMARY

Described herein generally are polymeric stents and methods for forming and/or manufacturing polymeric stents. A method of forming a polymeric stent can comprise: forcing a prepolymer solution onto a surface, for example, of a tube; initiating polymerization of the prepolymer solution to form a polymeric tube on the surface; and removing the polymeric tube from the tube it was formed within. The polymeric tube can optionally be modified using techniques described herein. In one embodiment, the polymer tube is modified by laser cutting the tube into a shape and/or pattern that can be used as a polymeric stent. In other embodiments, the surface can be textured and thereby forming a polymeric stent directly without the need for modification.

In another embodiment, the polymeric stents can be prepared by laser cutting a stent pattern into a polymeric tube of an appropriate length, machined to appropriate specifications, etched into a desired pattern, or a combination thereof. Such a polymeric tube can be created by forcing a prepolymer solution onto a surface of a tube; initiating polymerization of the prepolymer solution to form a polymeric tube on the surface; and removing the polymeric tube from the tube. Stents can be laser cut entirely from the polymeric tube or only portions of the polymeric tube can be laser cut. In other words, a combination of molding techniques and laser cutting can be used to form a final polymeric stent.

In another embodiment, the surface can be a textured surface and/or can have a cross-hatched pattern. Embodiments can have the forcing accomplished using centripetal force supplied when the tube is spun along a transverse axis. Other embodiments can have the forcing accomplished by injecting the prepolymer solution around the tube when the tube fits inside a second tube.

In other embodiments, the tube substantially fits within the second tube. The textured surface can also fit against an inner surface of the tube, and prepolymer can be injected into voids created by the textured surface between the tube and the second tube.

In one embodiment, the prepolymer solution can comprise a monomer, a macromer and a crosslinker. In other embodiments, the prepolymer solution comprises a monomer and a crosslinker. Initiating polymerization of the prepolymer solution can be accomplished using heat and/or ultraviolet light.

In some embodiments, the prepolymer solution comprises, and the final polymer can be formed from, alkyl methacrylate, ethylene glycol dimethacrylate, and ethoxylated trimethylol propane triacrylate. In other embodiments, the prepolymer solution comprises alkyl methacrylate, pentaerythritol triacrylate, and ethoxylated trimethylol propane triacrylate. Further still, in other embodiments, the prepolymer solution comprises alkyl methacrylate, di(trimethylol propane)tetraacrylate, and ethoxylated trimethylol propane triacrylate. In some embodiments, the prepolymer solution comprises alkyl methacrylate, di(trimethylol propane)tetraacrylate, hydroxyethyl methacrylate and ethoxylated trimethylol propane triacrylate. In other embodiments, the prepolymer solution comprises alkyl methacrylate, divinyl benzene, hydroxyethyl methacrylate and ethoxylated trimethylol propane triacrylate. In yet other embodiments, the prepolymer solution comprises alkyl methacrylate, ethylene glycol dimethacrylate, isopropyl alcohol and ethoxylated trimethylol propane triacrylate.

Also described herein are methods of forming a polymeric stent comprising: distributing a prepolymer solution onto an inner surface of a tube using centripetal force; initiating polymerization of the prepolymer solution using heat; forming a polymeric tube on the inner surface; removing the polymeric tube from the tube; and laser cutting a pattern into the polymeric tube thereby forming a polymeric stent.

Further described are methods of forming a polymeric stent comprising: distributing a prepolymer solution onto an outer textured surface of a tube by injecting a prepolymer solution between the outer textured surface and the inner surface of a second tube fit substantially around the outer textured surface; initiating polymerization of the prepolymer solution using heat; forming a polymeric stent on the outer textured surface; and removing the polymeric stent from the tube.

Also, described herein are methods of forming a polymeric stent comprising: distributing a prepolymer solution onto an inner textured surface of a tube by injecting a prepolymer solution between the inner textured surface and an outer surface of a second tube fit substantially inside the inner textured surface; initiating polymerization of the prepolymer solution using heat; forming a polymeric stent on the inner textured surface; and removing the polymeric stent from the tube.

Methods of forming polymeric stents are described comprising: distributing a prepolymer solution onto an inner surface of a tube using centripetal force; initiating polymerization of the prepolymer solution using heat and/or ultraviolet light; forming a polymeric tube on the inner surface; removing the polymeric stent from the tube; and laser cutting a stent pattern into the polymeric tube.

Also described herein are methods of forming polymeric stents comprising: distributing a prepolymer solution into a mold of a tube; initiating polymerization of the prepolymer solution using heat and/or ultraviolet light; forming a polymeric tube on the inner surface; removing the polymeric stent from the tube; and laser cutting a stent pattern into the polymeric tube.

Polymeric stents comprising various reaction products of combinations and concentrations of prepolymer solution components comprising alkyl methacrylate, ethylene glycol dimethacrylate, ethoxylated trimethylol propane triacrylate, pentaerythritol triacrylate, di(trimethylol propane) tetraacrylate, hydroxyethyl methacrylate, divinyl benzene, and isopropyl alcohol are also described.

DETAILED DESCRIPTION

Figure 1A:
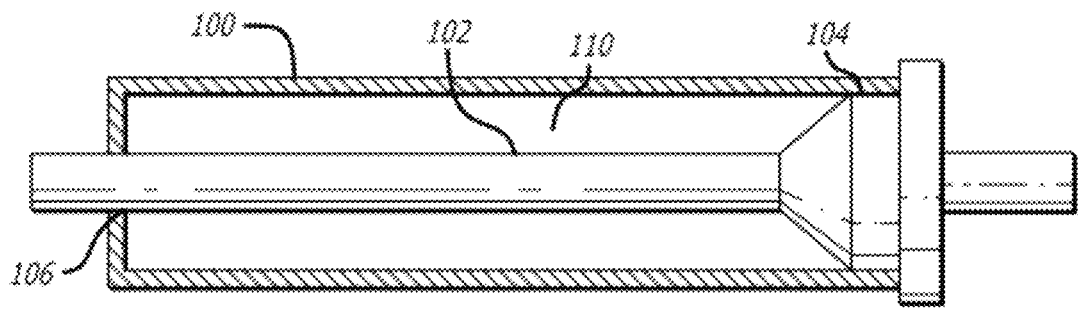
FIGS. 1A-1D illustrate steps in an example polymeric stent manufacturing technique.

Described herein are stents formed of and/or from polymeric materials. Methods of forming those stents are also described. It should be understood that these stents can be used alone or in combination with other stent components, such as inner coatings, outer coatings, inner layers, outer layers, anchoring members, catheters, microcatheters and the like. These additional stent components can also be composed of a polymer or any other type of material.

The stent embodiments disclosed herein can be substantially composed of a polymer. Polymers can include hydrogels, acrylates, PET (Dacron), nylon, polyurethane, Teflon, or PGA/PGLA.

The polymeric stents can be manufactured by polymerization of a prepolymer solution within a case, tube or mold of a desired shape. Generally, a liquid prepolymer solution can be delivered to a container of a desired shape, optionally processed, and then polymerized using a method described herein.

In some embodiments, the polymerized article can then be laser cut with or into an appropriate configuration, pattern, shape or a combination thereof. In other embodiments, the prepolymer solution can be polymerized in a mold of a particular configuration, pattern, shape or a combination thereof.

The prepolymer solution can include at least one monomer and/or a macromer and/or a crosslinker. The prepolymer components listed herein can be used to form the final polymer, and as such, the final polymers can be reaction products of the components listed.

The prepolymer solutions can comprise monomer(s) in a concentration from about 5% to about 80%, about 10% to about 70%, about 20% to about 60%, about 30% to about 50%, about 10%, about 20%, about 30%, about 40%, about 50%, about 60%, about 70% or about 80% w/w or any percentage within those listed or any range formed by one of the values.

The prepolymer solutions can comprise macromer(s) in a concentration from about 5% to about 80%, about 10% to about 70%, about 20% to about 60%, about 30% to about 50%, about 10%, about 20%, about 30%, about 40%, about 50%, about 55%, about 60%, about 70% or about 80% w/w or any percentage within those listed or any range formed by one of the values.

The prepolymer solutions can comprise crosslinker(s) in a concentration from about 5% to about 30%, about 10% to about 20%, about 5%, about 7%, about 10%, about 12%, about 15%, about 17%, about 20%, about 22%, about 25%, about 27%, or about 30% w/w or any percentage within those listed or any range formed by one of the values.

In some embodiments, acrylic monomers or macromers can be used in the prepolymer solution for polymer formation. In some instances, monomer selection can be guided by the desire to produce a more crystalline, rather than amorphous, copolymer, or in some instances a more amorphous copolymer may be desired. In other embodiments, polymer formulations can be tightly crosslinked networks prepared from hydrophobic monomers and crosslinkers.

Hydrophobic monomers used to form the polymeric stent can include an acrylate such as an alkyl acrylate hydroxyalkyl acrylate, alkyl alkacrylate or hydroxyalkyl alkacrylate. Acrylates can include, but are not limited to methyl methacrylate, hydroxyethyl methacrylate, hydroxypropyl methacrylate, hydroxybutyl methacrylate, tert-butyl acrylate, ethyl acrylate, derivatives thereof and combinations thereof.

Macromers can also be used to impart physical properties to the polymeric stents. Macromers can include ethoxylated trimethylol propane triacrylate, ethoxylated trimethylol propane triacrylate, ethoxylated trimethylol propane triacrylate 604, ethoxylated trimethylol propane triacrylate 428, or combinations thereof.

Crosslinkers can include N,N'-methylene bisacrylamide, divinyl benzene, ethylene glycol dimethacrylate, ethylene glycol diacrylate, and derivatives thereof. Other crosslinkers can include acrylate, methacrylate, or acrylamide derivatives of ethoxylated trimethylol propane, ethoxylated pentaerythritol, polyethylene glycol, polypropylene glycol, polytetramethylene oxide, di-ethoxylated trimethylol propane, ethoxylated glycerol, propoxylated glycerol, trimethylol propane, pentaerythritol, and glycerol.

In some embodiments, the prepolymer solution comprises alkyl methacrylate (e.g. methyl methacrylate), ethylene glycol dimethacrylate, and ethoxylated trimethylol propane triacrylate. In another embodiment, the prepolymer solution comprises alkyl methacrylate, pentaerythritol triacrylate, and ethoxylated trimethylol propane triacrylate. The prepolymer solution can also comprise alkyl methacrylate, di(trimethylol propane) tetraacrylate, and ethoxylated trimethylol propane triacrylate. Prepolymer solutions comprising alkyl methacrylate, di(trimethylol propane) tetraacrylate, hydroxyethyl methacrylate and ethoxylated trimethylol propane triacrylate are also contemplated. In other embodiments, the prepolymer solution comprises alkyl methacrylate, divinyl benzene, hydroxyethyl methacrylate and ethoxylated trimethylol propane triacrylate. A prepolymer solution can also comprise alkyl methacrylate, ethylene glycol dimethacrylate, isopropyl alcohol and ethoxylated trimethylol propane triacrylate.

Some of the monomers and crosslinkers are liquids with common miscibility. In some embodiments, a solvent can be required to dissolve the compounds or desired to control the mechanical properties of the resulting polymer. Any solvent in which the polymerizable compounds are soluble can be used. Solvents can include isopropyl alcohol, water, and methanol.

In some embodiments, thermoset polymers and co-polymers can be used. In one embodiment, the polymeric stent can be prepared from acrylic monomers and macromers.

Polymerization of the prepolymer solution can be by any convenient mechanism. The polymerization can be initiated by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the prepolymer solution. The selected initiator can be dissolved into the prepolymer solution or may remain as particulate.

After polymerization as described, the polymer stent or polymer tube can be he removed from the reaction vessel, washed, laser cut if needed, sterilized and prepared for use.

The polymeric stents can have a hydrated radial force of about 1 gf to about 50 gf, about 5 gf to about 40 gf, about 10 gf to about 30 gf, about 1 gf, about 2 gf, about 5 gf, about 8 gf, about 10 gf, about 11 gf, about 13 gf, about 15 gf, about 18 gf, about 20 gf, about 22 gf, about 25 gf, about 27 gf, about 30 gf, about 35 gf, about 36 gf, 2±1 gf, 8±1 gf, 11±1 gf, 18±1 gf, 22±1 gf, 27±4 gf, 36±2 gf or any radial force within the values listed.

Once formed, the polymer stent in an expanded configuration can have a diameter from about 2 mm to about 25 mm, about 2.5 mm to about 20 mm, about 5 mm to about 15 mm, about 7 mm to about 12 mm, about 2 mm, about 4 mm, about 6 mm, about 8 mm, about 10 mm, about 12 mm, about 14 mm, about 16 mm, about 18 mm, about 20 mm, about 22 mm, about 24 mm, about 25 mm, about 26 mm or any diameter within or between the listed values. This diameter can be changed by changing the size of the tube used to form the polymeric stent.

In order to deploy the polymeric stent, it can be collapsed onto a catheter. The collapsed polymeric stent can have a diameter from about 0.5 mm to about 6 mm, from about 1 mm to about 5 mm, from about 2 mm, to about 4 mm, about 0.5 mm, about 1 mm, about 1.5 mm, about 2 mm, about 2.5 mm, about 3 mm, about 3.5 mm, about 4 mm, about 4.4 mm, about 5 mm, about 5.5 mm, about 6 mm, or any diameter within or between the listed values. The stent can be collapsed onto a catheter having a size from about 0.021 Fr to about 22 Fr, about 0.05 Fr to about 8 Fr, about 0.5 Fr to about 4 Fr, about 0.020 Fr, about 0.05 Fr, about 0.05 Fr, about 1 Fr, about 2 Fr, about 5 Fr, about 10 Fr, about 15 Fr, about 16 Fr, about 20 Fr, about 22 Fr, or any size within or between these values.

Polymeric stents described herein can have lengths of about 5 mm to about 50 mm, about 10 mm to about 40 mm, about 20 mm to about 30 mm, about 5 mm, about 10 mm, about 15 mm, about 20 mm, about 25 mm, about 30 mm, about 35 mm, about 40 mm, about 45 mm, about 50 mm or any length within or between these values or any range made from those values. In one embodiment, the polymeric stents can have a length between about 10 mm and about 40 mm.

Polymeric stents in some cases need to be as thin as possible while still exhibiting appropriate structural properties, such as but not limited to, radial force. Polymeric stents described herein can have thicknesses of about 10 μm to about 300 μm, about 50 μm to about 250 μm, about 100 μm to about 200 μm, about 10 μm, about 25 μm, about 50 μm, abut 75 μm, about 100 μm, about 125 μm, about 150 μm, about 175 μm, about 200 μm, about 225 μm, about 250 μm, about 275 μm, about 300 μm, or any thickness within or between these values or any range made from those values. In one embodiment, a polymeric stent can have a thickness of about 150 μm.

The sizes of both the expanded diameter and the collapsed diameter can be tailored based on the size of the vessel to which the stent is delivered. The polymeric stents described herein can be used in vessels sized from small neuro vessels to coronary arteries to abdominal aorta.

One example of a polymer stent manufacturing technique is illustrated in FIGS. 1A-1D. In FIG. 1A, a generally cylindrical mandrel 102 is placed within tube 100. Mandrel 102 can create a fluid-tight seal on at least one end 104 of tube 100. In some embodiments, opposing end 106 of tube 100 is also closed and sealed.

Figure 1B:
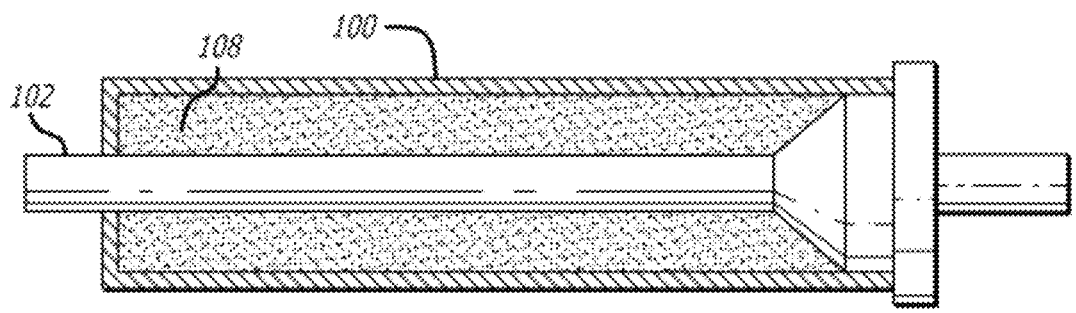
Figure 1C:
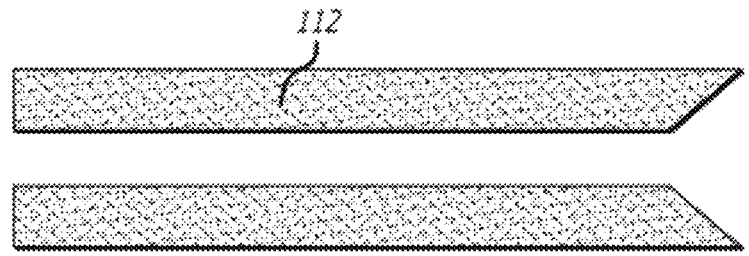
Figure 1D:
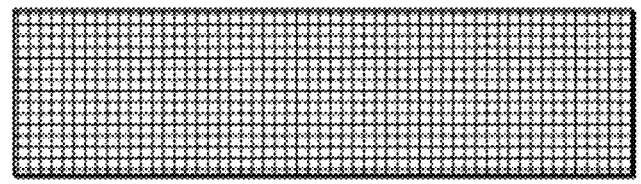

In FIG. 1B, liquid prepolymer 108 is injected into the space 110 created between mandrel 102 and tube 100. Polymerization is induced in prepolymer solution 108 (e.g., heating at 40-80° C. for 12 hours). Once polymerized, tube 100 and mandrel 102 are removed thereby leaving solid polymer tube 112, shown in FIG. 10. Tube 112 can be washed to eliminate residual monomers and dried over a mandrel to maintain shape. The polymer tube 112 can then be modified by laser cutting, computer numerical control (CNC) machining, etching or otherwise shaped into a desired pattern, such as the pattern seen in FIG. 1D.

Virtually any pattern can be etched, machined or laser cut into or on the polymeric tube during or after the manufacturing process. For example, the length and thickness of the final stent can be modified during the manufacturing process by changing the inner diameter or length of tube 100 or the outer diameter or length of mandrel 102, or both. If a larger diameter stent is required for a particular procedure, the outer diameter of mandrel 102 can be increased as well as about an identical increase in inner diameter of tube 100. The opposite can be performed to create a polymeric stent that has a narrower diameter. Also, in some embodiments, an entire stent pattern can be etched, machined or laser cut into a polymeric tube manufactured as described herein.

Figure 2:
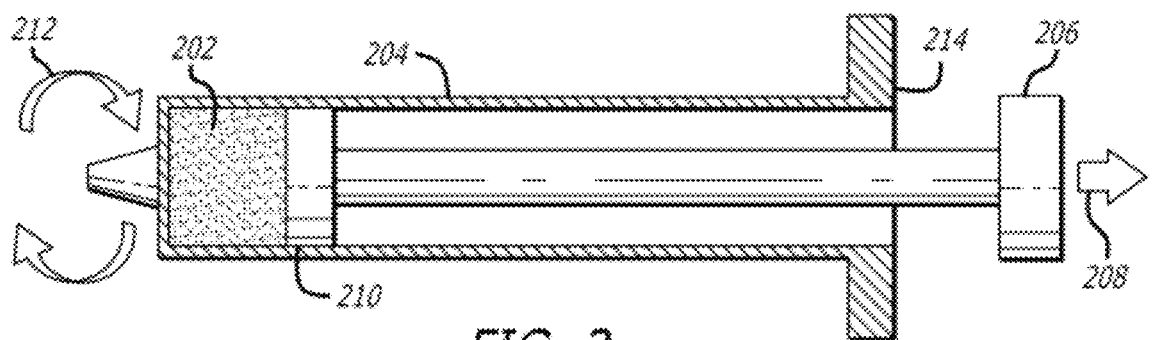
FIG. 2 illustrates an additional manufacturing process involving spinning the prepolymer filled tube.

Another example of a polymeric stent manufacturing process is illustrated in FIG. 2. Centrifugal force can be used to disperse prepolymer solution 202 along the inside of syringe tube 204. In one embodiment, plunger 206 can be positioned in the tube 204 and an amount or a predetermined amount of prepolymer solution 202 can be taken into syringe tube 204. Plunger 206 can be advanced back 208, causing plunger head 210 to move relative to the syringe tube portion filled with prepolymer solution. Syringe tube 204 may be connected to a mechanism that causes syringe tube 204 to spin 212 in a horizontal orientation (e.g., an overhead stirrer positioned horizontally with its rotating member connected to syringe tube 204).

Once syringe tube 204 achieves a sufficient rotational speed, plunger 206 may be pulled away from end 214 of syringe tube 204 (plunger head 210 toward end 214, taking in air. Since the prepolymer solution can now have more space to spread out, the centrifugal force causes an even coating to form on the wall of syringe tube 204. Polymerization can be initialed using a heat source and then heated (e.g., 40-80° C. for 12 hours). The solid polymer tube can then be removed from syringe tube 204, washed to eliminate residual monomers, dried on a mandrel, and then laser cut, CNC machined. etched or otherwise shaped into a desired pattern.

Sufficient rotational speed can be any speed that allows for the desired stent thickness resulting from centripetal force. For example, sufficient rotational speed can be about 100 rpm to about 2500 rpm, about 500 rpm to about 1500 rpm, about 1000 rpm to about 1500 rpm, about 100 rpm, about 200 rpm, about 300 rpm, about 400 rpm, about 500 rpm, about 600 rpm, about 700 rpm, about 800 rpm, about 900 rpm, about 100 rpm, about 1100 rpm, about 1200 rpm, about 1300 rpm, about 1400 rpm, about 1500 rpm, about 1600 rpm, about 1700 rpm, about 1800 rpm, about 1900 rpm, about 2000 rpm, about 2100 rpm, about 2200 rpm, about 2300 rpm, about 2400 rpm, about 2500 rpm, or any rotational speed or range of rotational speeds encompassed by the listed values. In one embodiment, the rotational speed is 1500 rpm.

In some embodiments, the air taken in during manufacturing can be argon, nitrogen, helium or even a gas that can aid in polymerization of the prepolymer solution.

The heat source can include a heat gun(s), a heated inner mandrel, a heated outer tube, a heated plunger, heated air, heated jacket, a heated chamber or any combination thereof.

A third method is illustrated in FIGS. 3A-F. In this process, turning first to FIG. 3A, a plastic and/or degradable rod 302 is placed in tube 304 and first luer adapter 306 and second luer adapter 308 can be connected to the openings at first end 310 and second end 312 of tube 304. Rod 302 can have an engraved or depressed pattern (e.g., created by laser machining, CNC machining or other suitable method) on its outer surface in the pattern desired for the final polymeric stent or any portion thereof. Also, the engraved or depressed portions can be partial in that they can aid in preparation for post formation etching or machining.

When rod 302 is placed in tube 304, these patterns or texture can form channels between the outer surface of rod 302 and the inner surface of tube 304 that are later filled by prepolymer solution. In some embodiments, the channels formed between the outer surface of rod 302 and the inner surface of tube 304 can be all that is filled with prepolymer solution to form the final stent. In other embodiments, prepolymer solution can be filled beyond the channels to form a more solid stent structure with an etched or depressed surface.

In another embodiment, the patterns or texture can reside on the inner surface of tube 304, and rod 302 has a flat surface. Here, these patterns or texture form channels between the outer surface of rod 302 and the inner surface of tube 304 in an opposite fashion. These channels can be later filled by prepolymer solution.

Figure 3A:
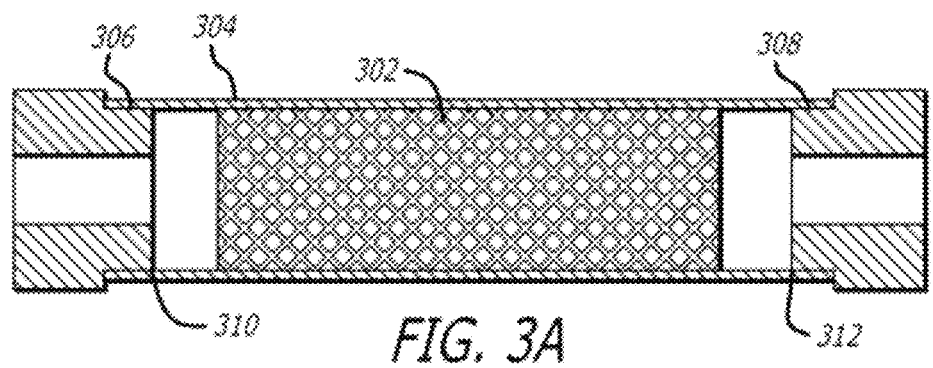
FIGS. 3A-F illustrate steps in another example polymeric stent manufacturing technique.
Figure 3B:
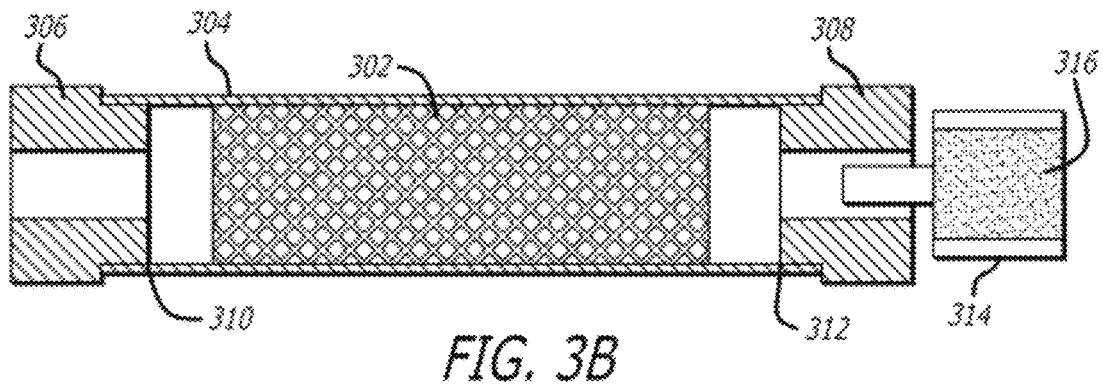
Figure 3C:
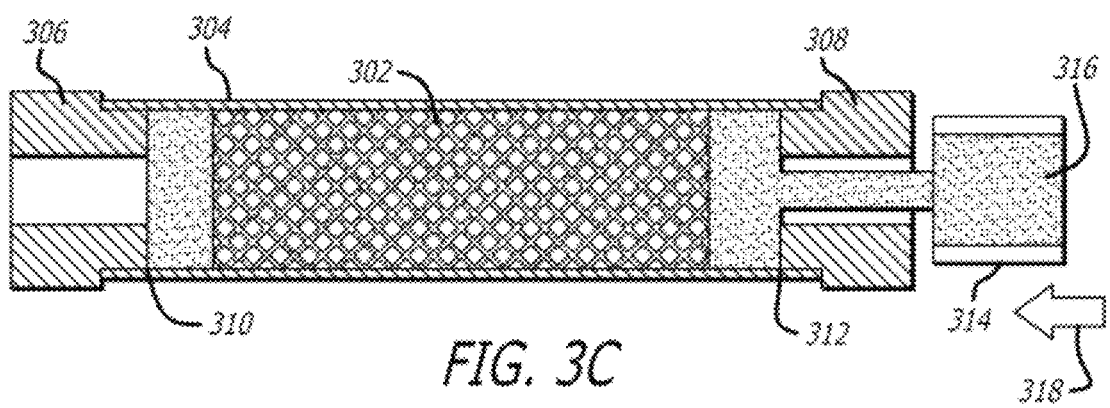

Next, as seen FIG. 3B, syringe 314 can be inserted into second luer adapter 308 and prepolymer solution 316 is injected 318 into the tube 304 as illustrated in FIG. 3C. In some embodiments, a syringe is used to introduce prepolymer solution, and in other embodiments, an injection channel can continuously deliver prepolymer solution as needed. Prepolymer solution 316 can fill into the pattern on the surface of rod 302. Syringe 314 can be removed from second luer adapter 308 and polymerization can be completed by heating prepolymer solution 316 (e.g., 40-80° C. for about 12 hours).

Figure 3D:
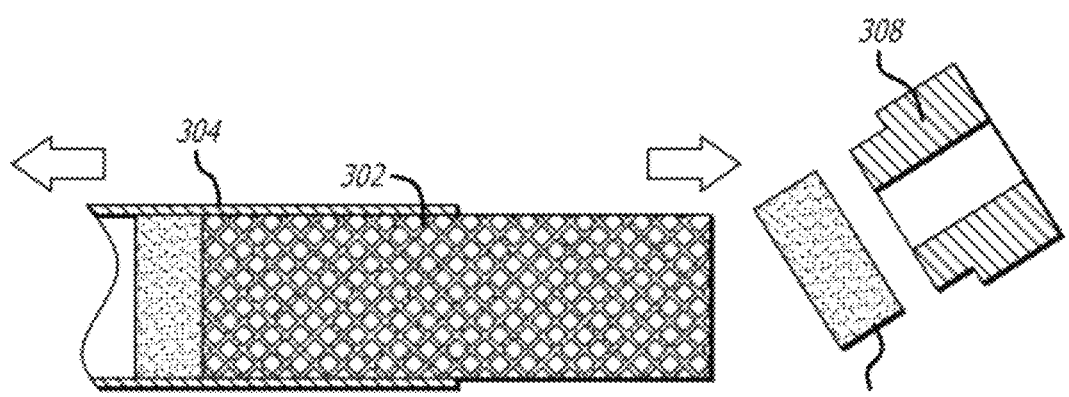
Figure 3E:
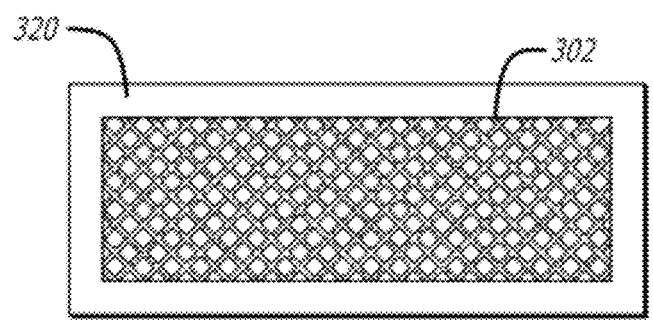
Figure 3F:
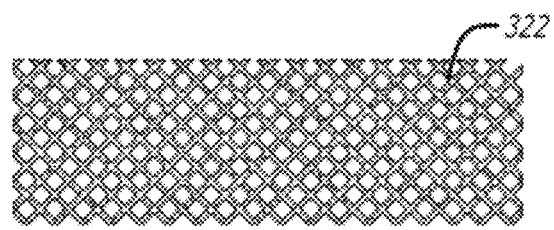

Then, second luer adapter 308 can be removed from tube 304 and rod 302 can be removed (e.g. slid) from the tube 304 as illustrated in FIG. 3D. Also, excess portion 318 can be machined off the remainder of the structure. Rod 302, the channels of which are filled with polymerized polymer, can be placed in an organic solvent bath 320 as illustrated in FIG. 3E. The organic solvent bath 318 can dissolve rod 302, leaving only polymer stent 322 (FIG. 3F) having the same pattern as the surface of rod 302.

In one embodiment, rod 302 can be formed of a polyester material. Rod 302 can be dissolved in solution of phenol in chloroform (e.g. 20%). After the rod is dissolved, the phenol solution can be exchanged with chloroform and washed again. Rinses with other liquids such as ethanol or methanol can also be performed. The stent can be dried after dissolution of rod 302. There may be different rod solvent combinations that can achieve the same result or a similar result that can be used.

It should be noted that different aspects of polymer stent 322 can be controlled by changing the pattern on the surface of the rod 302, the outer diameter of rod 302 and the inner diameter of tube 304, the length of rod 302 and tube 304 and similar dimensions. Additional modification can also be possible by laser cutting, CNC machining, etching, or similar processes.

Heating times and temperatures for the methods described herein can vary depending on the polymers used, machines used, heating sources, localized heating, or the like. Generally, the temperature used can be a temperature that does not substantially degrade the polymer forming the stent. Also, the heating can be slow and gradual or quick and elevated as long as the polymer is sufficiently cured after the heating process.

The polymeric stents themselves once manufactured can be used for different medical procedures. For example, the stents can be used in lumens throughout the body. Since the polymeric stents are biocompatible, they can be used in virtually any lumen.

Figure 4:
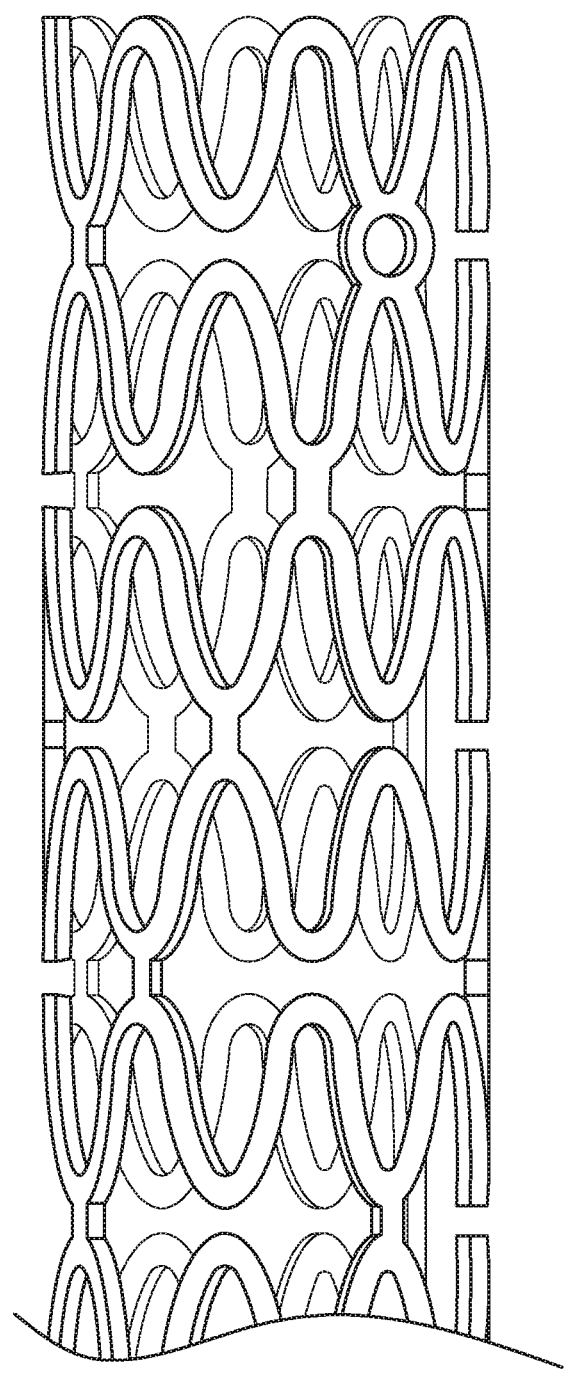
FIG. 4 illustrates a polymeric stent.
Figure 5:
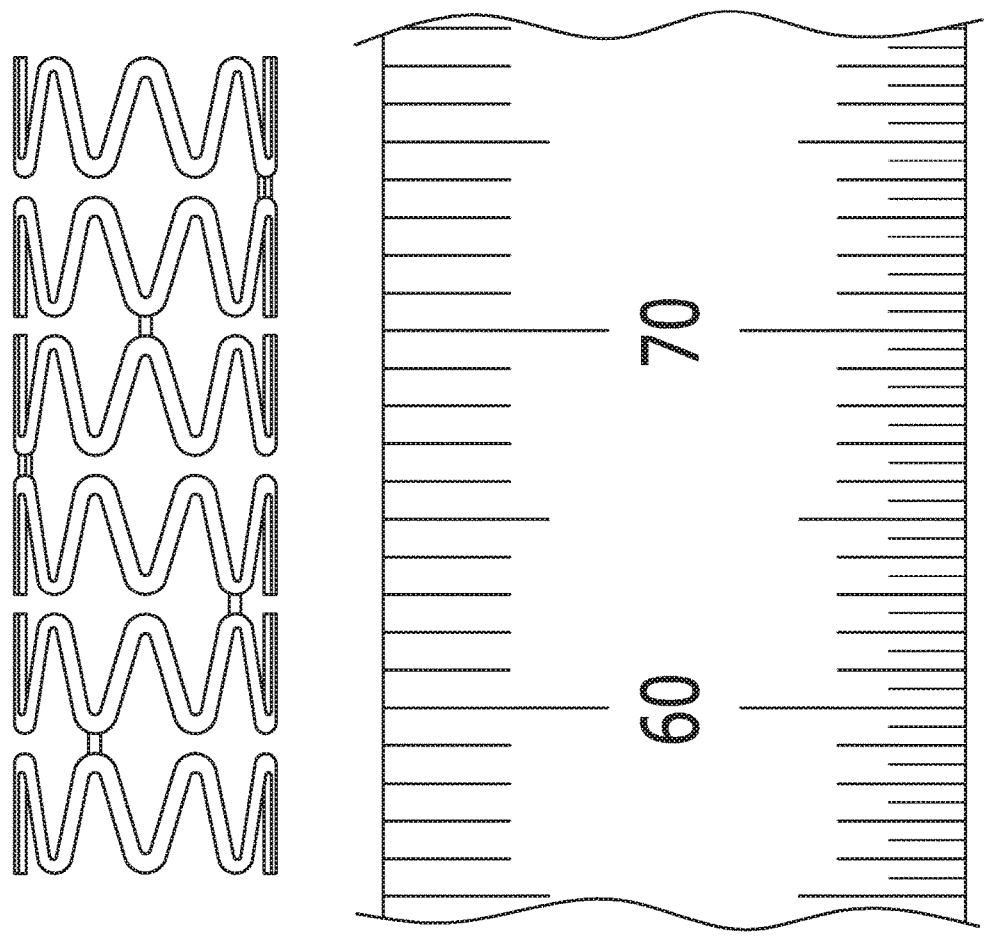
FIG. 5 illustrates another polymeric stent.

FIG. 4 illustrates an example structure of a polymer stent that can be used as a "coil assist" stent to maintain one or more microcoils within an aneurysm. In this example, the stent can be composed of a hydrogel that expands when exposed to certain fluids, however, any polymer can be used. This example hydrogel stent can be seen in its expanded form in FIG. 5. For reference, this polymeric stent is about 22 cm long in its expanded state.

Figure 6:
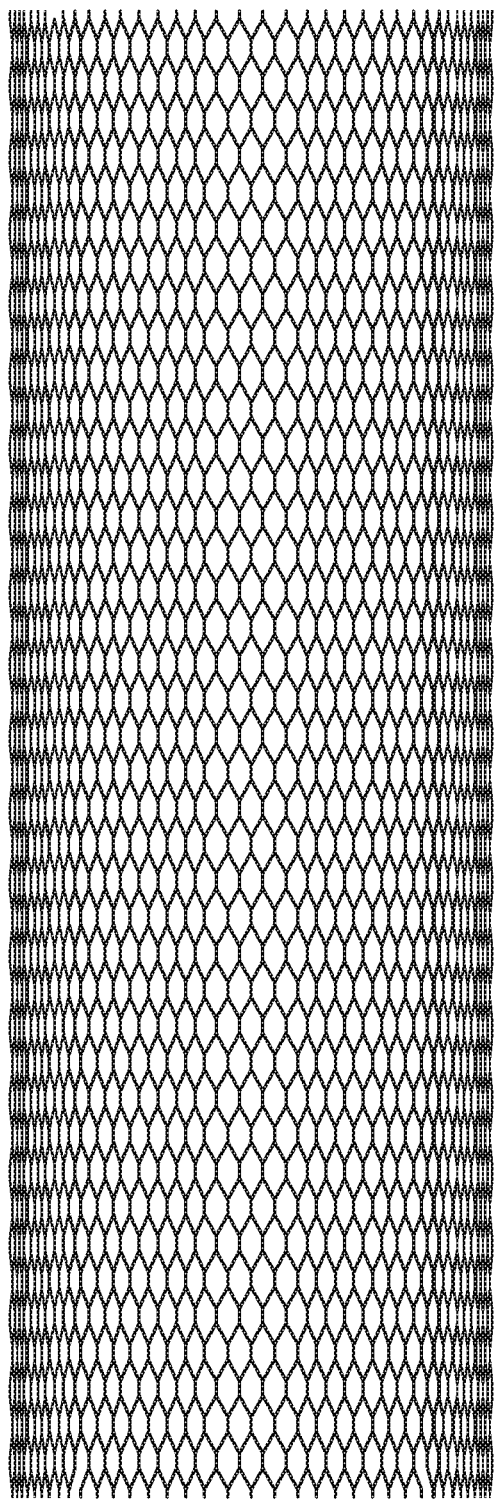
FIG. 6 illustrates an example structure of a polymer stent that can be used as a flow diverter for an aneurysm to divert blood flow from entering the aneurysm.
Figure 7:
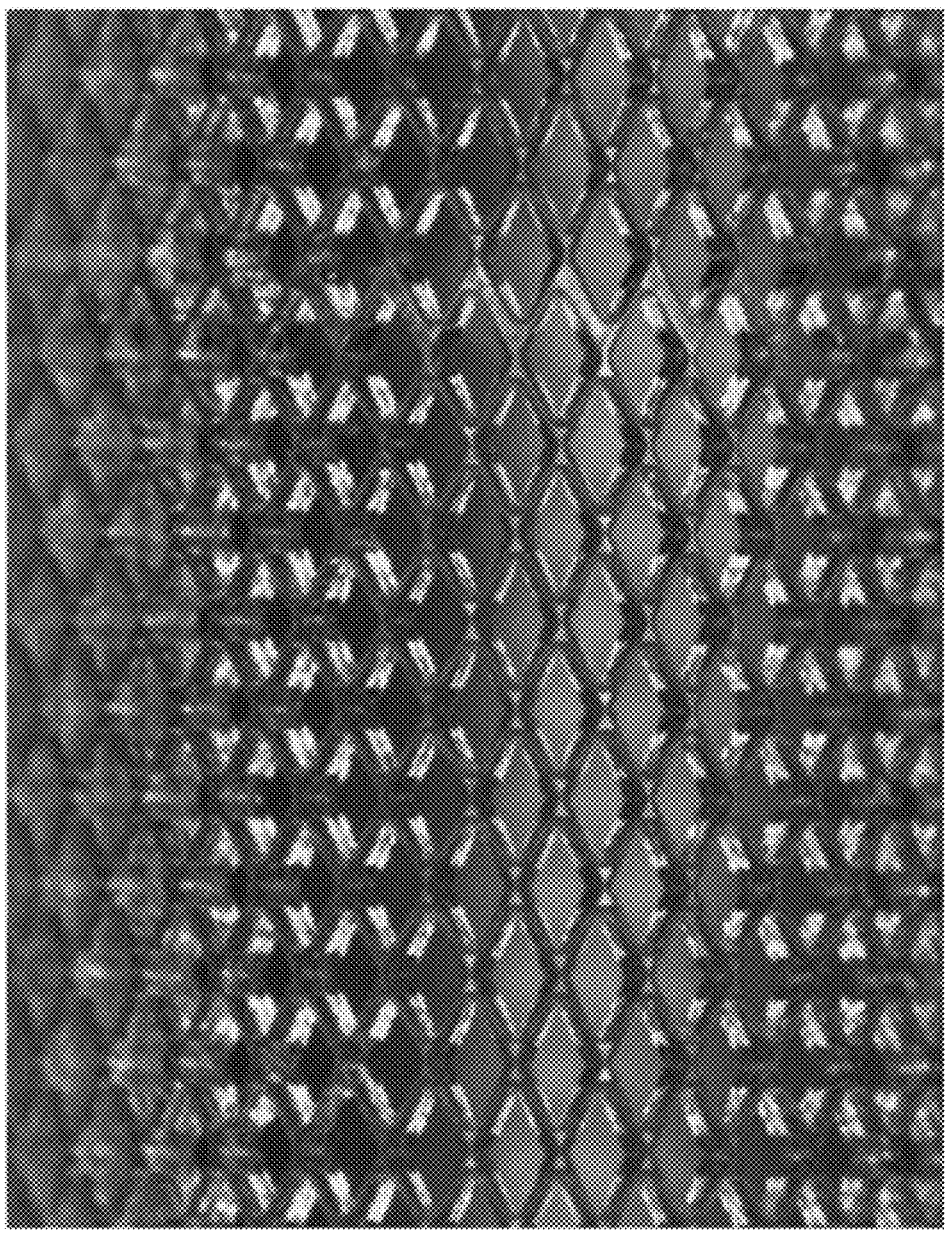
FIG. 7 illustrates a magnified view of a flow diverter polymeric stent.

FIG. 6 illustrates an example structure of a polymer stent that can be used as a flow diverter for an aneurysm to divert blood flow from entering the aneurysm. This flow diverter stent can be used alone or attached to another stent (e.g., the stent of FIGS. 4 and 5) as an additional layer. FIG. 7 illustrates a magnified view of the pattern of the flow diverter stent in FIG. 6. This example stent can also be composed of hydrogel that expands when exposed to certain fluids, however, any polymer can be used.

EXAMPLE 1

Preparation of Polymer Stents Utilizing the Molding Method

A prepolymer solution was prepared by combining 0.5 g methyl methacrylate, 0.5 g ethylene glycol dimethacrylate, 1.5 g ethoyxlated trimethylol propane triacrylate 604, and 40 mg 2,2'-azobis(2-methylpropionitrile) in a vial and mixing until solids were dissolved.

The mold was prepared by removing the plunger of a 1 mL polycarbonate syringe and placing a cap on the Luer-Lok fitting. A Grilamide tube (0.137" ID×0.183" OD) was inserted into the syringe cavity. The prepolymer solution (0.2 mL) was pipetted and a mandrel (3.1 mm OD) was inserted into the syringe cavity. The mold assembly was placed at 65° C. for 2.5 hrs. Following polymerization, the Grilamide tube was removed from the syringe and the mandrel was removed from the Grilamide tube. The polymer tube was placed at 65° C. for 12 hrs to fully polymerize. Finally, the Grilamide tube was scored and peeled away, leaving the polymer tube. The polymer tube was subsequently laser-cut to produce a finished polymer stent.

EXAMPLE 2

Preparation of Polymer Stents Utilizing the Spinning Method

A prepolymer solution was prepared by combining 0.5 g methyl methacrylate, 0.5 g ethylene glycol dimethacrylate, 1.5 g ethoyxlated trimethylol propane triacrylate 604, and 40 mg 2,2'-azobis(2-methylpropionitrile) in a vial and mixing until all solids were dissolved.

The mold was prepared by removing the plunger of a 1 mL polycarbonate syringe. A Grilamide tube (0.137" ID×0.183" OD) was inserted into the syringe cavity. After trimming the plunger, it was re-inserted into the syringe cavity to prevent the prepolymer solution from leaking out of the mold. The prepolymer solution (0.1 mL) was pipetted into the syringe cavity through the Luer-Lok fitting of the syringe and then the Luer-Lok fitting was capped. The syringe was placed in an overhead stirrer and rotated at 2,500 rpm. The mold was treated with hot air from a heat gun set at 100° C. for 1 hr to polymerize the polymer tube. Finally, the Grilamide tube was scored and peeled away, leaving the polymer tube. The polymer tube was subsequently laser-cut to produce a finished polymer stent.

EXAMPLE 3

Preparation of Polymer Stents Utilizing an Alternative Formulation

A prepolymer solution was prepared by combining 0.5 g methyl methacrylate, 0.5 g ethylene glycol dimethacrylate, 1.5 g ethoyxlated trimethylol propane triacrylate 604, 0.25 g isopropyl alcohol, and 40 mg 2,2'-azobis(2-methylpropionitrile) in a vial and mixing until all solids were dissolved.

The mold was prepared by removing the plunger of a 1 mL polycarbonate syringe and placing a cap on the Luer-Lok fitting. A Grilamide tube (0.137" ID×0.183" OD) was inserted into the syringe cavity. The prepolymer solution (0.2 mL) was pipetted and a mandrel (3.1 mm OD) was inserted into the syringe cavity. The mold assembly was placed at 65° C. for 2.5 hrs. Following polymerization, the Grilamide tube was removed from the syringe and the mandrel was removed from the Grilamide tube. The polymer tube was placed at 65° C. for 12 hrs to fully polymerize. Finally, the Grilamide tube was scored and peeled away, leaving the polymer tube. The polymer tube was subsequently laser-cut to produce a finished polymer stent.

EXAMPLE 4

Characterization of Polymer Stents of Different Formulations

The procedures detailed in Examples 1 and 2 were utilized to prepare polymer tubes of various chemical compositions that were subsequently laser-cut to produce polymer stents. The radial force of the polymer stents was determined using an Instron materials tester. Each stent was placed in 37° C. phosphate buffered saline and a probe was placed on stent. The probe travelled 1 mm and maximum compressive load was recorded. The test was repeated three times per stent, with the stent rotated 60 degrees between evaluations. The average and standard deviation of the radial force measurements are listed in the table below.

| Formulation | Prepolymer Composition (w/w) | Radial Force, Hydrated (gf) |
|---|---|---|
| 1 | 20% methyl methacrylate<br>20% ethylene glycol dimethacrylate<br>60% ethoxylated trimethylol propane triacrylate 604 | 18 ± 1 |
| 2 | 60% methyl methacrylate<br>10% ethoxylated trimethylol propane triacrylate 428<br>30% pentaerythritol triacrylate | 36 ± 2 |
| 3 | 60% methyl methacrylate<br>10% hydroxyethyl methacrylate<br>20% di(trimethylol propane) tetraacrylate<br>10% ethoxylated trimethylol propane triacrylate 604 | 27 ± 4 |
| 4 | 50% methyl methacrylate<br>10% hydroxyethyl methacrylate<br>20% di(trimethylol propane) tetraacrylate<br>20% ethoxylated trimethylol propane triacrylate 428 | 22 ± 1 |
| 5 | 20% methyl methacrylate<br>30% hydroxyethyl methacrylate<br>10% divinyl benzene<br>40% ethoxylated trimethylol propane triacrylate 428 | 11 ± 1 |
| 6 | 40% methyl methacrylate<br>10% hydroxyethyl methacrylate<br>10% divinyl benzene<br>40% ethoxylated trimethylol propane triacrylate 428 | 18 ± 1 |
| 7 | 50% methyl methacrylate<br>10% hydroxyethyl methacrylate<br>20% di(trimethylol propane) tetraacrylate<br>20% ethoxylated trimethylol propane triacrylate 604 | 22 ± 1 |
| 8 | 20% methyl methacrylate<br>20% ethylene glycol diacrylate<br>60% ethoxylated trimethylol propane triacrylate 604 | 8 ± 1 |
| 9 | 18% methyl methacrylate<br>18% ethylene glycol dimethacrylate<br>55% ethoxylated trimethylol propane triacrylate 604<br>9% isopropyl alcohol | 2 ± 1 |

EXAMPLE 5

Preclinical Evaluation of Polymer Stent in Rabbit Iliac

Figure 8:
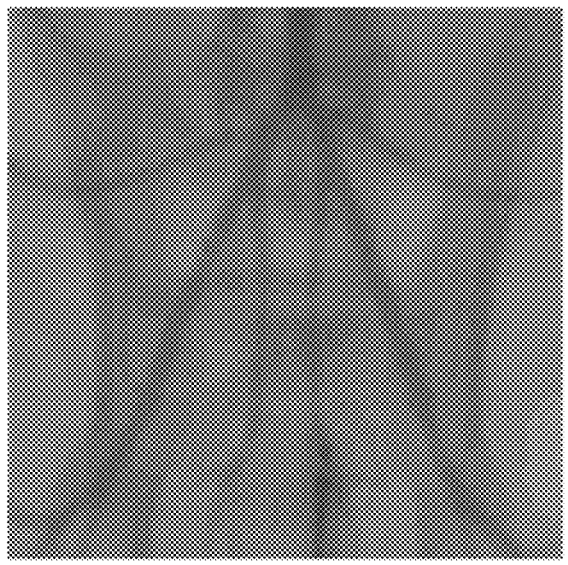
FIG. 8 illustrates good blood in all both iliac arteries in a rabbit 28 days after implantation of a polymeric stent made according to Example 1.
Figure 9:
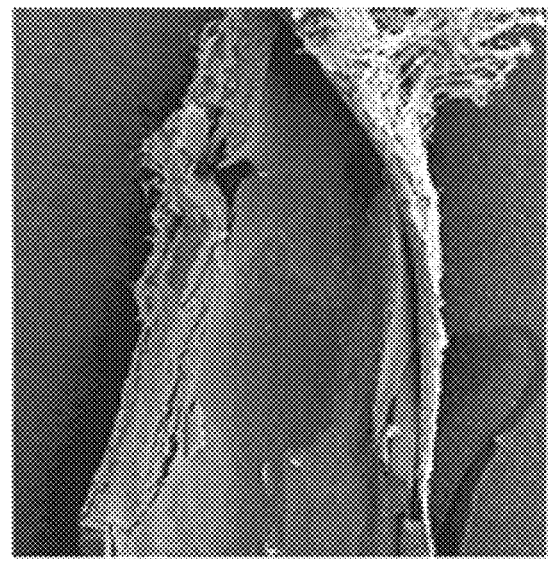
FIG. 9 illustrates a scanning electron microscope image of the arteries imaged in FIG. 8.
Figure 10:
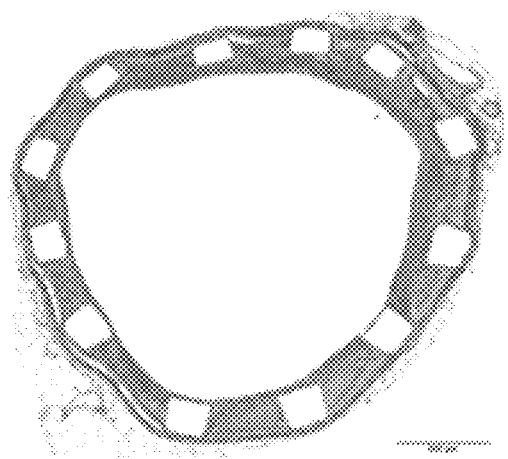
FIG. 10 illustrates a histology sample of an artery held open using a polymeric stent made according to Example 1.

The polymer stent of Example 1 was evaluated in the iliac arteries of three rabbits. After laser-cutting, the polymer stent was compressed over a plastic tube that would permit passage of a 0.014" guide wire and loaded into the distal end of a 5 Fr guide catheter (Chaperon, MicroVention, Inc., Tustin, Calif.). The 5 Fr guide catheter was advanced from the carotid artery to the iliac artery and deployed using a pusher. After deployment and at the 28 day follow-up angiography (FIG. 8), good blood flow was observed in all six iliac arteries. The arteries were harvested and evaluated using scanning electron microscopy (FIG. 9) and histology (FIG. 10). The histological sample illustrated in FIG. 10 demonstrates that a polymeric stent of Example 1 can hold open a vessel.

EXAMPLE 6

Preclinical Evaluation of Polymer Stent in Rabbit Sidewall Aneurysms

Figure 11:
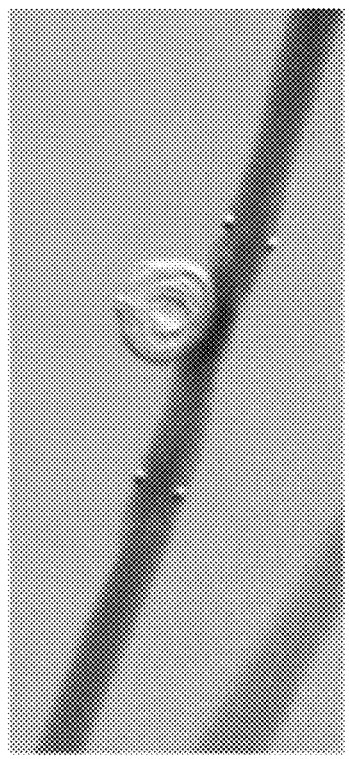
FIG. 11 illustrates a three month post polymeric stent insertion angiogram of a carotid artery of a rabbit. The vein pouch aneurysm was treated with all-polymer embolic devices.
Figure 12:
FIG. 12 illustrates a three month post polymeric stent insertion MR reconstruction of the carotid artery of the rabbit from FIG. 11.
Figure 13:
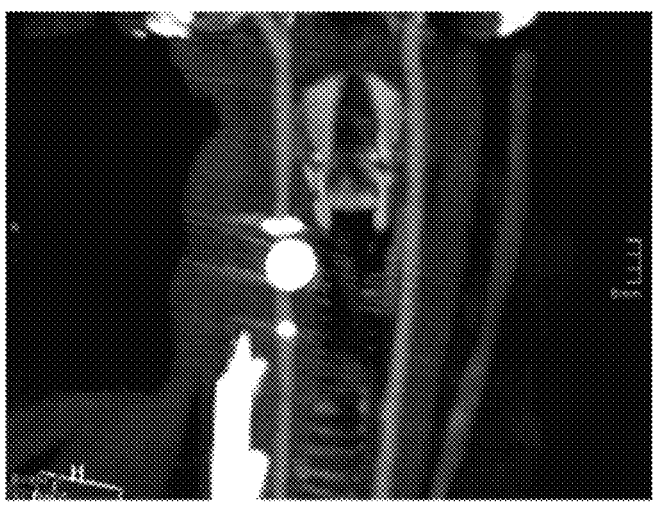
FIG. 13 illustrates a three month post polymeric stent insertion CT angiography of the carotid artery of the rabbit from FIG. 11.
Figure 14:
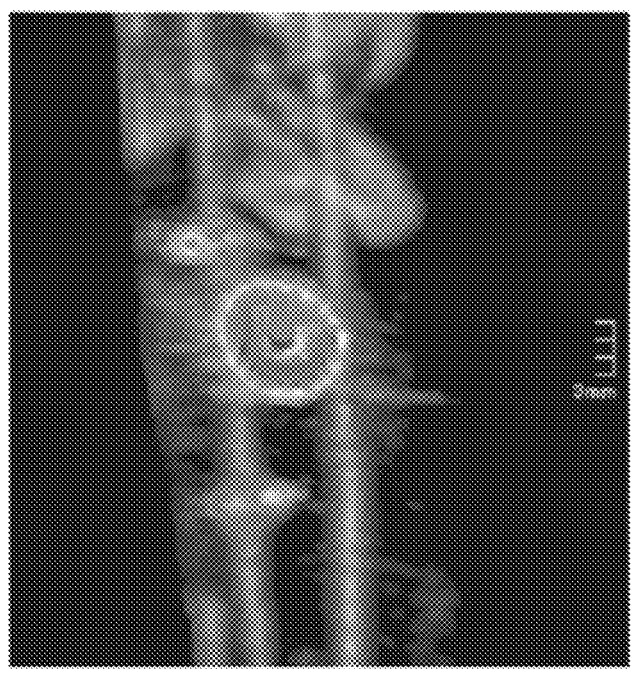
FIG. 14 illustrates a three month post polymeric stent insertion CT reconstruction of a carotid artery of a rabbit.
Figure 15:
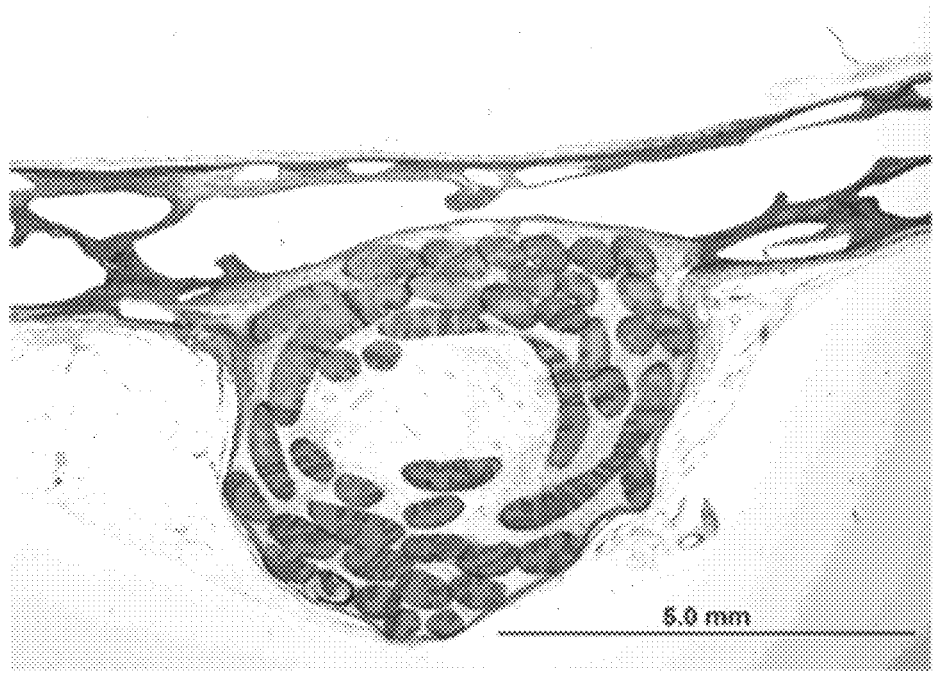
FIG. 15 illustrates a three month post polymeric stent histology sample of a carotid artery of the rabbit of FIG. 11 showing the stent aiding in keeping the vessel open and the coils in the aneurysm.

The polymer stent of Example 1 was placed over the neck of sidewall aneurysms attached to the carotid artery of six rabbits. After laser-cutting, the polymer stent was compressed and loaded into the distal end of a 5 Fr guide catheter (Chaperone, MicroVention, Inc., Tustin, Calif.). After embolization of the aneurysm, a 6 Fr guide catheter (Chaperone) was advanced to a point just distal of the aneurysm. The 5 Fr stent-loaded guide catheter was advanced through the 6 Fr guide catheter and deployed using a pusher. Three months post-treatment, the aneurysms were evaluated using angiography (FIG. 11), MR reconstruction (FIG. 12), CT angiography reconstruction (FIG. 13), CT (FIG. 14) and histology (FIG. 15). Subsequently, the arteries were harvested and evaluated using scanning electron microscopy or histology.

FIGS. 11-14 illustrate lack of blood flow to the aneurysm yet blood flow remaining through the carotid artery where the stent had been implanted across the region of the aneurysm. The histological sample in FIG. 15 illustrates that the stent can have sufficient radial strength, and it can aid in keeping the vessel open and blood flowing.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of forming a polymeric stent comprising:
preparing a prepolymer solution comprising a macromer, a monomer and a crosslinker, wherein the macromer includes ethoxylated trimethylol propane triacrylate;
forcing the prepolymer solution onto a textured surface of a first tube wherein the forcing is accomplished by injecting the prepolymer solution into voids created by the textured surface of the first tube and an inner surface of a second tube when the first tube fits inside the second tube and the textured surface of the first tube fits against the inner surface of the second tube;
initiating polymerization of the prepolymer solution to form a polymeric tube on the textured surface; and
modifying the polymeric tube into a desired shape or pattern, wherein the formed polymeric stent has a hydrated radial force of about 1 gf to about 50 gf.

2. The method according to claim 1 wherein the textured surface has a cross-hatched pattern.

3. The method according to claim 1 wherein the first tube substantially fits within the second tube.

4. The method according to claim 1 wherein the modifying comprises laser cutting the polymeric stent to an appropriate length.

5. The method according to claim 1 wherein initiating polymerization of the prepolymer solution is accomplished using heat.

6. The method according to claims 1 wherein initiating polymerization of the prepolymer solution is accomplished using ultraviolet light.

7. The method according to claim 1 wherein the prepolymer solution comprises at least one of alkyl methacrylate, ethylene glycol dimethacrylate, ethoxylated trimethylol propane triacrylate, pentaerythritol triacrylate, di(trimethylol propane) tetraacrylate, hydroxyethyl methacrylate, divinyl benzene, isopropyl alcohol or a combination thereof.

8. A method of forming a polymeric stent comprising:
preparing a prepolymer solution comprising a macromere, a monomer and a cross linker, wherein the macromere includes ethoxylated trimethylol propane triacrylate;
distributing the prepolymer solution onto an outer textured surface of a tube by injecting the prepolymer solution between the outer textured surface and the inner surface of a second tube fit substantially around the outer textured surface wherein the outer textured surface of the tube fits against the inner surface of the second tube;
initiating polymerization of the prepolymer solution using heat;
forming a polymeric stent on the outer textured surface; and
removing the polymeric stent from the tube, wherein the formed polymeric stent has a hydrated radial force of about 1 gf to about 50 gf.

9. A method of forming a polymeric stent comprising:
preparing a prepolymer solution comprising a macromere, a monomer and a cross linker, wherein the macromere includes ethoxylated trimethylol propane triacrylate;
distributing the prepolymer solution onto an inner textured surface of a tube by injecting the prepolymer solution between the inner textured surface and an outer surface of a second tube fit substantially inside the inner textured surface wherein the inner textured surface fits against the outer surface of the second tube;
initiating polymerization of the prepolymer solution using heat;
forming a polymeric stent on the inner textured surface; and
removing the polymeric stent from the tube, wherein the formed polymeric stent has a hydrated radial force of about 1 gf to about 50 gf.

* * * * *